(12) United States Patent
Pascal et al.

(10) Patent No.: US 9,410,087 B2
(45) Date of Patent: Aug. 9, 2016

(54) FUNGICIDAL AND PARASITICIDAL FIRE-RETARDANT POWDER

(71) Applicant: SOLVAY SA, Brussels (BE)

(72) Inventors: Jean-Philippe Pascal, Villers les Nancy (FR); Olivier Patat, Paris (FR); Magali Riglet, Viroflay (FR)

(73) Assignee: SOLVAY SA, Brussels (BE)

( * ) Notice: Subject to any disclaimer, the term of this patent is extended or adjusted under 35 U.S.C. 154(b) by 0 days.

(21) Appl. No.: 14/410,274

(22) PCT Filed: Jun. 26, 2013

(86) PCT No.: PCT/EP2013/063442
§ 371 (c)(1),
(2) Date: Dec. 22, 2014

(87) PCT Pub. No.: WO2014/001417
PCT Pub. Date: Jan. 3, 2014

(65) Prior Publication Data
US 2015/0368560 A1    Dec. 24, 2015

(30) Foreign Application Priority Data
Jun. 26, 2012 (EP) .................................... 12305748

(51) Int. Cl.
C09K 21/04    (2006.01)
C04B 28/02    (2006.01)
C04B 40/00    (2006.01)
D21H 21/34    (2006.01)
D21H 21/36    (2006.01)
A01N 59/04    (2006.01)
C04B 103/63   (2006.01)
C04B 103/67   (2006.01)

(52) U.S. Cl.
CPC ............... *C09K 21/04* (2013.01); *A01N 59/04* (2013.01); *C04B 28/02* (2013.01); *C04B 40/0039* (2013.01); *D21H 21/34* (2013.01); *D21H 21/36* (2013.01); *C04B 2103/63* (2013.01); *C04B 2103/67* (2013.01); *Y02W 30/97* (2015.05)

(58) Field of Classification Search
CPC .... C04B 14/06; C04B 14/066; C04B 18/241; C04B 22/10; C04B 22/106; C04B 22/12; C04B 22/124; C04B 22/128; C04B 22/147; C04B 22/149; C04B 22/16; C09K 21/04; D21H 21/34; D21H 21/36
See application file for complete search history.

(56) References Cited

U.S. PATENT DOCUMENTS

| 2,881,138 | A |   | 4/1959  | Reiss |
| 3,903,337 | A |   | 9/1975  | Yamamoto et al. |
| 4,038,451 | A |   | 7/1977  | Brown et al. |
| 4,168,175 | A | * | 9/1979  | Shutt .................... C08K 3/32 106/15.05 |
| 4,182,681 | A |   | 1/1980  | Gumbert |
| 4,251,579 | A |   | 2/1981  | Lee et al. |
| 4,468,495 | A | * | 8/1984  | Pearson ................ C08G 12/40 106/18.14 |
| 4,909,328 | A |   | 3/1990  | DeChant et al. |
| 4,994,113 | A |   | 2/1991  | Helmstetter |
| 5,833,874 | A |   | 11/1998 | Stewart et al. |
| 5,909,776 | A | * | 6/1999  | Stewart ................ A62C 35/10 169/26 |
| 5,938,969 | A | * | 8/1999  | Morton ................ A62D 1/0014 252/4 |
| 7,045,476 | B1 |  | 5/2006  | Lally |
| 2009/0320717 | A1 | * | 12/2009 | Adams ................ C04B 40/0039 106/18.11 |

FOREIGN PATENT DOCUMENTS

| EP | 0543349 A1 | 5/1993 |
| JP | 49-33880 B | 9/1974 |
| JP | 61-05856 A | 1/1986 |
| RU | 2216371 C2 | 11/2003 |
| RU | 2370295 C2 | 10/2009 |
| WO | WO 91/00326 A1 | 1/1991 |
| WO | WO 2009135973 A1 | 11/2009 |
| WO | WO 2012/085218 A1 | 6/2012 |

OTHER PUBLICATIONS

[Author Unknown]—"CIMA Technical Bulletin #1, Cellulose insulation: codes, regulations, and specifications", 1998, The Cellulose Insulation Manufacturers Association, Dayton, OH, US, Dec. 1998; 5 pgs; accessed online on Apr. 9, 2013 at http://www.cellulose.org/userdocs/TechnicalSpecifications/CIMA-TechnicalBulletin01.pdf.

[Author Unknown]—NEOBOR® Product Data Sheet, "$Na_2B_4O_7 5H_2O$ Sodium Tetraborate Pentahydrate, Borax 5 Mol, Neobor Pentahydrate Borax, Technical Grade: Granular and Powder", Dec. 2007, Rio Tinto Minerals, 3 pgs; accessed online on Apr. 10, 2013 at http://www.borax.com/docs/product_pdfs_data/pds-borates-neobor.pdf?sfvrsn=.

Shirtliffe, C.J., et al.—"Blown Cellulose Fiber Thermal Insulations: Part 2—Thermal Resistance" 1978, Thermal Transmission Measurements of Insulation, ASTM Special Technical Publication 660, pp. 104-129; 29 pgs.

* cited by examiner

*Primary Examiner* — Anthony J Green
(74) *Attorney, Agent, or Firm* — Beatrice C. Ortego

(57) ABSTRACT

Fire-retardant powder comprising at least 30% by weight of mono ammonium dihydrogen phosphate and/or di-ammonium monohydrogen phosphate, at least 5% by weight of alkaline bicarbonate, at least 3% by weight of silica, and at least 5% by weight of a compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc (II) chloride, and combinations thereof. The invention also relates to building materials preferably comprising natural fibers and comprising at least 5% by weight, and at most 30% of a powder according to the invention.

23 Claims, No Drawings

FUNGICIDAL AND PARASITICIDAL FIRE-RETARDANT POWDER

CROSS-REFERENCE TO RELATED CASES

This application is a U.S. national stage entry under 35 U.S.C. §371 of International Application No. PCT/EP2013/063442 filed Jun. 26, 2013, which claims priority to European application No. 12305748.1 filed on Jun. 26, 2012, the whole content of this application being incorporated herein by reference for all purposes.

TECHNICAL FIELD

The invention relates to a fire-retardant powder. It relates more particularly to a fungicidal and parasiticidal fire-retardant powder presenting good smoke inhibitor properties that can be used in building materials, in particular building materials based on natural fibers. It also relates to building materials containing this fire-retardant powder.

The expression 'fire-retardant powder' is understood to mean a powder which, used in combination with an inflammable material, makes it possible to slow down or even inhibit the combustion of the inflammable material as measured for example by the EN ISO 11925-2 standard.

The expression 'smoke-inhibitor powder' is understood to mean a powder which, used in combination with a flammable material, makes it possible to reduce or even inhibit the smoke generation when said flammable material is subjected to a flame or to partial combustion as measured for example by the ASTM E1354-02 standard.

The expression 'fungicidal powder' is understood to mean a powder in contact with which fungi and moulds (fungi such as *Aspergillus* in particular *Aspergillus fumigatus* and *Aspergillus niger, Cladosporium* in particular *Cladosporium fulvum* and *Cladosporium sphaerospermum, Penicilliums* in particular *Penicillium brevicompactum* and *Penicillium alteraria*), which have a tendency to grow in building materials, in particular on natural fibers, cannot survive.

The expression 'parasiticidal powder' is understood to mean a powder in contact with which parasites (arthropods such as darkling beetles, weevils, lice, fleas, acarids, and xylophagous insects such as mites, longhorn beetles, termites), which have a tendency to grow in building materials, in particular on natural fibers, cannot survive. The parasites may be in the egg, larval or adult stage.

The action of the powder as fungicide or parasiticide may be direct. It may also be indirect, for example when the powder destroys a substance necessary to the survival of the fungus or parasite.

The expression 'natural fiber' is understood to mean a fiber:
  of plant origin such as flax, flax shives, hemp, stalk of peeled hemp, jute, sisal, coir, cotton, and wood,
  or of animal origin such as wool, and feather.

The natural fiber may be virgin (first use) or recycled such as for example cotton (used clothing), or cellulose (old papers, boards), etc.

BACKGROUND ART

The combustible behaviour of building materials containing natural fibers is a well-known problem that has existed for a very long time. Indeed, since wood and cob have a low fire resistance, man has developed alternative building materials mainly made of mineral materials such as stones, clay bricks, concrete, and mineral wools that are less combustible. However, the carbon footprint of such structures is high, on the one hand due to the energy needed for the production of such materials (such as cements, bricks, blocks, rock wools), and on the other hand due to the energy cost of transporting such reputedly heavy and dense materials from their production sites to the building sites where they are used.

By signing the Kyoto agreements, many countries are committed to reducing their greenhouse gas emissions by a factor of four between now and 2050. Thus, for example, European Directives henceforth impose energy consumption limits on new buildings. These energy consumption limits take into account the entire life cycle of the building: namely, the energy for producing the building materials, the energy for transporting them, the energy for assembling them, the energy consumption for heating (winter) and cooling (summer) the premises, the energy for the demolition of the building and the treatment and transport of the corresponding waste.

Thus, there are many architects and building designers who wish to use greater quantities of novel building materials comprising fibers of natural origin within the context of sustainable development. Indeed, these novel materials have an intrinsic carbon dioxide storage capacity since they are made up of a high percentage of organic matter. Moreover, these novel materials generally use little energy for their manufacture, they are light, they have a low heat capacity and they can have excellent thermal or sound insulation properties when they are used in a sufficient thickness. Their energy balance and their greenhouse gas footprint, per square meter built, are thus highly favourable over the life cycle of the building.

However, their combustible property is a curb on their use for obvious reasons of occupational safety of the premises, and their biodegradable property, attractive for the sustainable development aspect, poses serious problems with respect to the sensitivity of these materials to attacks by parasites and moulds which often result in an accelerated degradation of the structure.

Moreover, the occupation of these building by people or animals also requires a neutrality of the materials used with respect to the allergy risks or health risks promoted for example by fungi, acarids and parasites such as fleas or ticks.

A large number of treatments are proposed in order to fireproof these novel materials comprising natural fibers. Mention may for example be made of: brominated compounds (such as polybrominated aromatic compounds, in particular decabromodiphenyl ether and tetrabromobisphenol), compounds based on boron salts (such as borates and in particular the hydrated salts of boric acid), phosphorus-containing compounds (such as, in particular, zinc phosphate, ammonium phosphate, and magnesium, zinc or zirconium polyphosphonates), nitrogen-containing compounds (such as ammonium sulfates and ammonium halides), salts of metal (aluminium, antimony, zinc) compounds.

U.S. Pat. No. 4,182,681 discloses a fire retardant composition in powder form consisting mainly of alkaline compounds such as borax (hydrated $Na_2B_4O_7$) 43 w. % base of boric acid, Ammonium sulfate (($NH_4)_2SO_4$) 31 w. %, Aluminium sulfate ($Al_2(SO_4)_3$) 19 w. %, alkaline Sodium carbonate ($Na_2CO_3$) 4 w %, Silica gel 1.3 w. %.

US2009/320717 discloses an alkaline fire retardant composition comprising a carbonate salt which is alkaline and one additional salt such as Borax ($Na_2B_4O_7.5H_2O$) which is also alkaline. The composition may comprise white sand along with Borax and Baking soda (example 2 respectively 40/40/20 parts, example 3 respectively 25/25/50 parts).

However, several of these fire-retardant compounds may present risks to the health of people handling these products during the manufacture of the building materials or to the health of the occupants of the buildings constructed with these compounds, or during the end-of-life treatment and recycling of the materials. Mention may for example be made of:

- among the fire retardants based on boric acid and boron salts certain national or even regional regulations (for example of the European Union) are changing to a CMR (carcinogenic, mutagenic and reprotoxic) classification of these substances,
- among brominated fire retardants: certain polybromobiphenyls or polybrominated diphenylethers which are the subject of regulatory restrictions in several regions of the world.

Among the components used as fungicide, mention may be made of organotin compounds, organometallic complexes, or the (ammonium, copper, zinc, etc.) salts of organic acids, sulfur-containing compounds (such as octylisothiazolinone).

Among the parasiticidal compounds, mention may be made of pyrethrins, set of natural substances derived from pyrethrum flowers, synthetic pyrethroids, benzoylureas, organophosphorus compounds and carbamates. These substances have the drawback of being neurotoxic both to parasites and to humans. These compounds should therefore be used with precaution in order to minimize the risks to the health of the staff manufacturing the treated materials, or the building construction staff, or the people occupying buildings comprising materials treated with such compounds.

SUMMARY OF THE INVENTION

These drawbacks are lessened or eliminated by the use of the fire-retardant powder according to the present invention. The invention is based on a new "3-in-1" fire-retardant, fungicidal, and parasiticidal protective fire-retardant powder that has a long-lasting fire-retardant, fungicidal and parasiticidal efficacy imparting also low smoke generation properties when applied to a combustible material and when said combustible material is exposed to fire. Moreover the fire-retardant powder is healthy for humans, and is environmentally friendly, by reducing the bio-impacts in all stages of the life cycle of materials comprising such a powder: both in their manufacturing phase and in the material utilization phases and also at the end of the cycle at end-of-life of the material.

It has surprisingly been observed that a Lewis acid such as monoammonium phosphate or diammonium phosphate, preferably monoammonium phosphate, could be mixed with a base of the alkaline bicarbonate type without neutralizing the fire-retardant properties of the acid and while retaining the fungicidal and parasiticidal properties of the alkaline bicarbonate. And that a compound selected from the group consisting of: sodium chloride, potassium chloride, potassium bromide, potassium sulfate, aluminium hydroxide, magnesium hydroxy-carbonate pentahydrate, magnesium chloride hexahydrate, ammonium sulfate, iron(II) sulfate heptahydrate, zinc(II) chloride, and combinations thereof, in combination with the mono or diammonium phosphate, the alkaline bicarbonate and silica in claimed proportion of present invention imparts particular interesting combined fire-retardant and smoke-inhibition properties when used in combustible materials, particularly in natural combustible materials.

Consequently, the invention relates to the use of a fire-retardant powder comprising at least 30% by weight of monoammonium phosphate and/or di-ammonium phosphate, preferably mono-ammonium phosphate, and at least 5% by weight of alkaline bicarbonate, and at least 3% by weight of silica, and at least 5% by weight of a compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof.

The invention relates also to the use as a smoke-inhibitor of a powder comprising at least 30% by weight of monoammonium phosphate and/or di-ammonium phosphate, preferably mono-ammonium phosphate, and at least 3% by weight of silica, and at least 5% by weight of a compound selected from the group consisting of: sodium chloride, potassium chloride, potassium bromide, potassium sulfate, aluminium hydroxide, magnesium hydroxy-carbonate pentahydrate, magnesium chloride hexahydrate, ammonium sulfate, iron(II) sulfate heptahydrate, zinc(II) chloride, and combinations thereof.

A first advantage of the powder according to the present invention is that it simultaneously exhibits fire-retardant, fungicidal and parasiticidal properties.

A second advantage of the powder according to the present invention is that it does not contain compounds capable of degrading the air quality of buildings utilizing building materials that contain this powder.

A third advantage of the powder according to the present invention is that it reduces the smoke generation in the event of partial combustion of the material that contains it.

A fourth advantage of the powder according to the present invention is that it enables to decrease the amount of fire retardant powder to a given material to reduce generated smoke and impart fire-resistance when the material is exposed to fire. Thus this may enable also to limit the loss of thermal resistance of such material.

A fifth advantage of the powder according to the present invention is that it enables to reduce the weight of the corresponding material incorporating such a fire-resistant powder.

A sixth advantage of the powder according to the present invention is that the addition of additives such as sodium chloride, potassium chloride, potassium bromide, potassium sulfate, magnesium carbonate hydroxide pentahydrate, magnesium chloride hexahydrate, iron(II) sulfate heptahydrate, or zinc(II) chloride enables to reduce the amount of monoammonium phosphate which is an expensive chemical compound replacing part of it with less expensive chemicals while improving the overall efficiency of the '3-in-1' fire-retardant powder.

A seventh advantage of the powder according to the present invention is that an improved smell (with a strongly reduced smell or no smell at all of ammonia) is detectable by human nose when it is used in natural materials comprising natural fiber.

An eighth advantage of the powder according to the present invention is that it minimizes the emission of odours of certain natural materials such as those comprising feathers and wool.

A ninth advantage of the powder according to the present invention is that, in the event of water leaching of the building material that contains it, during its life cycle, for example during the dismantling of the structure, certain major components such as the alkaline bicarbonate and the silica, or even all of the components, for example when the other components are chosen from food-grade salts, have a minimal impact in the natural environment: in particular the bicarbonate is a natural pH buffer, and the silica is a component that is widespread in nature. Furthermore, during the hydrolysis of the acidic monoammonium phosphate in the presence of water, the acidic chemical species discharged, according to Brönsted, are partially neutralized by the alkalinity of the sodium bicarbonate.

A tenth advantage of the powder according to the present invention is that, in the event of energy recovery from the building material at the end of its usage cycle, as a mixture for example with other combustible natural compounds, a portion of the major components (alkaline bicarbonate and silica) will release into the fumes only $CO_2$ and water originating from the thermal decomposition. Moreover, the presence of an alkaline bicarbonate will reduce the emission of highly acidic gases (for example $SO_3$, $SO_2$, HF, HCl, HBr, NOx, $P_2O_5$, etc.) if the building material comprises sulfur-containing materials, halides-containing materials, nitrogen-containing materials or phosphate-containing materials.

DESCRIPTION OF THE PREFERRED EMBODIMENTS

In the powder according to the invention the monoammonium phosphate is monoammonium dihydrogenphosphate ($NH_4H_2PO_4$), the diammonium phosphate is diammonium hydrogenphosphate (($NH_4)_2HPO_4$).

In the powder according to the invention, the alkaline bicarbonate may, for example, be bicarbonate in the strict sense such as potassium bicarbonate, sodium bicarbonate or ammonium bicarbonate. However, in this document it also covers compound salts such as alkaline sesquicarbonates (for example trona) which comprise bicarbonate and that presents a pH of at most 9.9, preferably at most 9.8 in water when at 0.1 mol/L concentration. Sodium or potassium bicarbonates or trona are especially suitable. Bicarbonates in the strict sense are recommended. Potassium bicarbonate or sodium bicarbonate, more particularly sodium bicarbonate, are preferred.

In the powder according to the invention, the silica may, for example, be silica in the strict sense such as anhydrous or hydrated silicon oxide, synthetic precipitated or pyrogenic silica. However, in this document it also covers silica compounds such as acid or alkaline silicates (such as sodium silicate, or sodium metasilicate), feldspars, diatomaceous earths, zeolites, phonolite, aluminium, magnesium or iron silicates, fuller's earth, talc ($Mg_3Si_4O_{10}(OH)_2$), mica, vermiculite, clays such as attapulgite (($Mg,Al)_2Si_4O_{10}(OH).4(H_2O)$), bentonite, montmorillonite, kaolin ($Al_2Si_2O_5(OH)_4$). Advantageously silica is selected from the group consisting of: precipitated silica, pyrogenic silica, phonolite, and combination thereof.

Precipitated silica, pyrogenic silica and the phonolite are especially suitable. Amorphous (non-crystalline) silicas are recommended.

The powder comprises at least 30%, advantageously at least 40%, more advantageously at least 50% by weight of monoammonium and/or diammonium phosphate, preferably at least 30%, advantageously at least 40%, more advantageously at least 50% by weight of monoammonium phosphate. Generally, the powder comprises at most 87%, advantageously at most 80%, more advantageously at most 70%, still more advantageously at most 60% by weight of ammonium phosphate.

The powder comprises at least 5% advantageously at least 7%, preferably at least 10% by weight of alkaline bicarbonate. Generally, the powder comprises at most 30%, advantageously at most 20%, more advantageously at most 15%, still more advantageously at most 13% by weight of alkaline bicarbonate.

In a certain other embodiment of the invention, the powder comprises at least 5% and less than 20% by weight of alkaline bicarbonate.

The powder comprises at least 3%, preferably at least 4%, more preferably at least 5% by weight of silica. The powder comprises generally at most 10%, preferably at most 9%, more preferably at most 8%, still more preferably at most 7% by weight of silica.

In present invention the fire-retardant powder comprises at least 5%, preferably at least 7%, more preferably at least 10%, and most preferred at least 20% by weight of a compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof. The fire-retardant powder comprises generally at most 62%, preferably at most 50%; more preferably at most 40%, still more preferably at most 30% by weight of such a compound or such combinations. Preferably the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, is the group consisting of: potassium chloride, potassium bromide, magnesium chloride hexahydrate, iron (II) sulfate heptahydrate, and combinations thereof.

In a particular advantageous embodiment of the powder of present invention, the alkaline bicarbonate is sodium bicarbonate, and the silica is precipitated or pyrogenic silica or phonolite, and the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, is the group consisting of: potassium chloride, potassium bromide, potassium sulfate, magnesium chloride hexahydrate, iron (II) sulfate heptahydrate, and combinations thereof.

In order to be free flowing, and to limit the reaction of the ammonium phosphate with the alkaline bicarbonate, the powder of present invention should have a limited content of water. The water content of the powder according present invention is advantageously at most 15%, preferably at most 10%, more preferably at most 5%, still more preferably at most 3% by weight. This enables also to limit the reaction of acidic monoammonium phosphate with the alkaline bicarbonates. In particular the water content that is caught by crystalline compounds or salts is not detrimental as far as the water is not released by melting of the crystals up to 70° C.

In one preferred embodiment of the invention, the fire-retardant powder comprises less than 2%, preferably less than 1%, more preferably less than 0.1% by weight of boron compound expressed as boron. In a more preferred embodiment of the invention, the fire-retardant powder is essentially free of boron salts and/or boron acid. Indeed boric acid and boron compounds are classified as reprotoxic for humans. One should understand by essentially free of boron salts or of boric acid, a fire-retardant powder without intended boron compounds added other than the natural boron content traces of the added compounds.

In another advantageous embodiment, the fire-retardant powder is free of other fire-retardant constituents capable of forming nitrogenous and/or potash fertilizers favourable to the growth of fungi and moulds.

According to a variant of the invention, the fire-retardant powder is even free of any other fire-retardant constituent.

In another variant, the powder is free of any other fungicidal constituents.

In a preferred embodiment, the powder is free of neurotoxic parasiticidal active principles. And in a more preferred embodiment, the powder is free of other parasiticidal active principles.

The ammonium phosphate (mono or di ammonium phosphate), the bicarbonate, the silica, and fourth compound (selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof) mixture must be as homogeneous as possible. It is recommended that the particle sizes of the ammonium phosphate, bicarbonate, silica, and fourth compound be similar in order to facilitate the mixing. The mixing may be carried out in any type of powder mixer known to those skilled in the art, such as blade mixers equipped with lifter blades. However, it has been observed that in certain circumstances, in particular when the mixing is carried out in ploughshare mixers, which is advantageous, too long a mixing time may lead to a loss of efficacy of the fire-retardant powder. In general, times longer than 10 minutes should be avoided. Generally, it is also recommended to mix the ammonium phosphate, bicarbonate, silica, and fourth compound mixture in such a way as to fluidize it. This fluidization takes place in a ploughshare mixer when the mixture falls back into the mixer following the rotation of the ploughshare.

The powder according to the invention, comprising a large portion or even a major portion by weight of constituents that are non-toxic to humans or animals, may be readily used in a large number of building materials, advantageously in building materials comprising natural fibers of plant origin such as flax, flax shives, hemp, stalk of peeled hemp, jute, sisal, coir, cotton, and wood, or of animal origin such as wool, and feather. The natural fibers are generally virgin or recycled natural fibers.

The powder according to the invention is advantageously used in the manufacture of material comprising cellulose wadding.

Another aspect of the invention relates to the use of a powder according to the invention for its combined fire-retardant, fungicidal and parasiticidal effects. Still another aspect of the invention relates to the use of a powder according to the invention as smoke-inhibitor.

Fibers to which the powder according to the present invention has been added may be used alone, for example in the form of loose-fill insulation or as a mixture with natural mineral mortars, or as a mixture with binders of, preferably natural, adhesive type before web formation and compaction, or as a mixture with plastics, preferably bioplastics such as polylactic acid (PLA), polyhydroxybutyrate (PHB), polyamide 11 derived from plant oil, bio-derived polyethylene (PE), bio-derived polyvinyl chloride (PVC), and composite mixtures thereof.

In a first particular embodiment, at least one of the components of the powder according to the present invention, preferably at least two components, more preferably at least three components, still more preferably at least four components chosen from the monoammonium phosphate or di-ammonium phosphate, the alkaline bicarbonate, the silica and the compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof, is (are) present in the form of particles having a weight-average diameter less than or equal to 100 µm, preferably less than or equal to 80 µm, more preferably less than or equal to 30 µm. The diameters are measured by laser diffraction and diffusion particle size analysis on a Malvern Mastersizer S particle size analyser via the liquid route, using an He—Ne laser source having a wavelength of 632.8 nm and a diameter of 18 mm, a measurement cell equipped with a backscatter 300 mm focal length (300 RF), an MS 17 liquid preparation unit, an automatic solvent filtration kit ('ethanol kit') using ethanol saturated with bicarbonate, according to the ISO 13320-2009 standard. The particle size distribution is that calculated as the volume distribution of the particles. This volume distribution is equivalent to a weight distribution for a given particle density.

According to one advantageous embodiment of the present invention, the manufacture of the powder comprises at least one step of simultaneous milling of at least two of the components of the powder chosen from the monoammonium dihydrogen phosphate or di-ammonium monohydrogen phosphate, the alkaline bicarbonate, the silica, the compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof. The co-milling of at least the alkaline bicarbonate and the silica is preferred. This co-milling makes possible an especially increased efficacy of the fire-retardant, fungicidal and parasiticidal properties. This co-milling phase may be carried out in any mill known to those skilled in the art, such as grinding mills, impact plate mills, hammer mills or pin mills. Pin mills are advantageous. Mills equipped with particle size selectors, which allow the internal recycling to the mill of the largest particles, are particularly advantageous.

In a second particular embodiment, at least one of the components of the powder according to the invention, preferably at least two components, more preferably at least three components, still more preferably at least four components chosen from the monoammonium dihydrogen phosphate or di-ammonium monohydrogen phosphate, the alkaline bicarbonate, the silica, the compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof, is (are) present in the form of particles having a weight-average diameter of at least 80 µm, preferably of at least 100 µm, more preferably still of at least 130 µm, and at most 500 µm, preferably at most 400 µm and more preferably still 300 µm. The diameters of the powder of this second particular embodiment are measured by screening through a sieve according to the ISO 3310-1:2000 standard. This particular embodiment allows easier processing in the case of the production of building materials comprising constituents, in particular natural fibers, which may be co-milled with the fire-retardant powder. This co-milling phase allows excellent mixing of the powder with the material while limiting the entrainment of the powder particles into the dust extraction devices placed level with and downstream of the mill.

The present invention also covers the use of monoammonium or diammonium phosphate and/or alkaline bicarbonate and/or silica for the manufacture of a fire-retardant powder according the present invention.

The present invention also relates to a method of manufacturing building material comprising virgin and/or recycled natural fibers and a powder according to the invention, the manufacturing method comprising a step of simultaneous milling of the natural fibers and of the powder according to the present invention.

Consequently, the present invention also relates to a building material, preferably comprising natural fibers and comprising the powder of the present invention.

To impart the related effects associated with the powder, the material should comprise a sufficient amount of powder. In present invention building materials, preferably comprising natural fibers, generally comprises at least 5% by weight, advantageously at least 6%, and more advantageously at least 8% of a powder of the invention. Indeed a too low content of monoammonium phosphate or diammonium phosphate in the building material is detrimental for the associated fire-retardant properties. Therefore the building material of the present invention comprises generally at least about 4.3%, advantageously at least about 5%, more advantageously at least about 7% by weight of monoammonium phosphate and/or diammonium phosphate, preferably of monoammonium phosphate.

In reverse too much fire-retarding powder in the material is often detrimental to mechanical or thermal properties of the material. Therefore, the building material of present invention, preferably comprising natural fibers, generally comprises at most 30%, advantageously at most 20%, more advantageously at most 17%, even more advantageously at most 14%, and still more advantageously at most 12% by weight of a powder of the invention.

When the building material of present invention comprises natural fibers, it generally comprises at least 10%, preferably at least 30%, more preferably at least 50%, even more preferably at least 70% by weight of natural fibers. Generally the building material comprises at most 95%, preferably at most 90% by weight of natural fibers.

In particular embodiments, the building material of present invention comprises or consists of cellulose wadding. Indeed cellulose wadding presents a number of advantages such as a low thermal conductivity and a low weight. It is easily integrated in panels, or in floor/wall/roof elements parts that can be assembled for constructions of buildings.

The following examples are intended only to exemplify the invention and are not intended to limit the scope of the claimed invention.

EXAMPLES

Example 1

Powder in Accordance with the Invention 3.4 kg of Thermphos food grade monoammonium dihydrogen phosphate, 0.4 kg of Solvay Bicar Z 0/50 sodium bicarbonate, 0.2 kg of silica of Solvay Rhodia Tixosil 38AB and 1.0 kg of VWR Prolabo Rectapur potassium chloride are taken.

Using four devices for metering solids by weight, the four powders are introduced simultaneously into a Hosokawa-Alpine UPZ 100 pin mill rotating at 17 000 rpm at a respective throughput of 1.7, 0.2, 0.1, and 0.5 kg/h of each powder.

A homogeneous powder is obtained comprising 68% by weight of monoammonium dihydrogen phosphate, 8% by weight of sodium bicarbonate 4% by weight of silica and 20% by weight of potassium chloride.

The particle size of the powder is such that the weight-average diameter is less than or equal to 80 p.m.

Example 2

In Accordance with the Invention

In this example, tests are carried out on various strains of pathogenic fungi of the human habitat (*Aspergillus niger, Cladosporium phaerospermum, Penicillium brevicompactum*) or lignivorous fungi (dry rot: *Serpula lacrymans*) in order to evaluate the fungicidal efficacy of the powder according to the present invention. For this purpose, the powder according to Example 1 was deposited directly on an agar medium inoculated with one of the following strains: *Aspergillus niger, Cladosporium sphaerospermum, Penicillium brevicompactum*, and *Serpula lacrymans*. The areas of inhibition, that is to say the areas where the growth of the fungi was stopped by the action of the powder, are very pronounced for each of the strains used.

Example 3

In Accordance with the Invention

Larvae of common European termites (*Reticulitermes lucifugus*), which are xylophagous insects, are used in order to evaluate the insecticidal efficacy of the powder according to the present invention. For this purpose, the powder according to Example 1 was mixed with cellulose fibers. Two powder doses are tested: 7% and 12% in the cellulose fibers. The mortality of *Reticulitermes lucifugus* is observed as a function of the time.

Example 4

In Accordance with the Invention

Larvae of clothes moths (*Tineola bisselliella*), which are keratophagous insects, are used in order to evaluate the insecticidal efficacy of the powder according to the present invention. For this purpose, the powder according to Example 1 was mixed with hemp fibers. Two powder doses are tested: 7% and 12% by weight mixed in the hemp fibers. The mortality of *Tineola bisselliella* is observed as a function of the time.

Example 5

In Accordance with the Invention

Manufacture of insulating cellulose wadding.

100 kg of old newspapers are taken. After sorting (removal of metals and plastics), the paper is milled in a first mill in order to shred the paper and reduce it to pieces the size of a postage stamp.

Using two solids metering devices (calibrated screw feeder) each equipped with a buffer hopper, the following:
  a powder composed of a mixture of monoammonium dihydrogen phosphate (composed of particles having a weight-average diameter between 80 and 200 μm), Solvay Bicar Z sodium bicarbonate and silica of Solvay Rhodia Tixosil 38AB type and potassium chloride of VWR Prolabo Rectapur in weight proportion of Example 1,
  and the paper shredded in the first step reduced to pieces the size of a postage stamp,
are introduced simultaneously into a second mill.

The second mill is placed just after the addition of the powder of additives.

The pieces of paper previously shredded and the powder added in a proportion of 10% by weight relative to the total mixture (powder plus paper) are finely and simultaneously reduced.

At the outlet of the mill, a fiber with a fluffy appearance is obtained that has many asperities and is soft to the touch, with good fixation and good homogeneity of the powder in the fibers. Its bulk density is 35 kg/m$^3$. Its thermal conductivity is about 0.038 W·m$^{-1}$·K$^{-1}$. Its specific heat capacity is about 1650 J/(kg·K).

A filtration system that enables the paper dust to be recovered makes it possible to verify that the initial powder is not entrained very much into the dust extraction circuits.

At the outlet of the second mill, the treated wadding is then weighed and compressed before being bagged.

The cellulose wadding thus treated is then used as thermal insulation in insulation thicknesses of 5 to 45 cm.

The amounts used are dependent on the installation techniques: by pneumatic blowing into wall compartments: 50 to 65 kg/m$^3$, by wet spraying: 30 to 50 kg/m$^3$, and by manual installation into wall compartments: 50 to 65 kg/m$^3$.

This additive-laden wadding has good resistance to fire, and to the growth of fungi and parasites.

Example 6

Comparison of the fire-retardant behaviour of various compositions in accordance or not with the present invention.

Various powder compositions using the same equipment and same operating conditions as Example 1 were used, using the raw materials listed at table 1.

Cellulose wadding was taken as an example of material that is representative of flame and fumes behaviour of materials comprising natural fibers. In this series of tests, a virgin cellulose wadding was taken and was co-grinded with different powder compositions with same operating conditions of the ones described in Example 5, using a UPZ 100 pin mill rotating at 7000 rpm.

The fire behaviour of various powder formulations listed at table 2 has been evaluated in a comparative manner according to a methodology adapted from the NF EN ISO 11925-2 standard: Reaction to fire—Ignitability of building products subjected to direct impingement of flame—Part 2: Single-flame source test.

A flame from a gas burner ref X2000PZ (Soudogaz) of 12 cm long wherein the internal blue part of the flame is set to 4 cm, is applied to the face of the material to be tested with an angle of 45° and at a distance of 2 cm from the end of the blue part of the flame to the tested material. After 5 seconds of flame exposition to the material, the burner is withdrawn, and a visual observation determines if there is ignition of the cellulose wadding, the time that the flame lasts for of the cellulose wadding (flame duration), the duration of burning (persistence of the zone of incandescence), and the surface area of the spread of the fire in % of the cellulose wadding. The results are moreover interpreted according to the observations made during the test on the nature of the burning (in particular whether it is deeply burned towards the thickness of the cellulose wadding, or superficially burned). The measured weight-loss of the material before and after flame exposition has been performed for most of the tests but they were not reported in present tables. Ranges of 30 to 72% of weight loss have been measured when visual observation assesses 'deeply burned' and ranges of 2% to 5% of weight loss of the material have been measured when visual observation assesses 'superficially burned'.

The smoke generation by the material exposed to flame was qualified in the results table according the following comparative levels:

Very light: observation of a few dispersed light fumaroles. The fumaroles disappear quickly with time during burning.

Light: observation of light fumaroles distributed over the entire surface of burning. The fumaroles disappear slowly during burning.

Medium: observation of a thin curtain of smoke on the entire surface of burning. This smoke persists throughout during burning.

Important: the smoke forms a curtain of thick smoke visible on the entire surface of burning. This curtain continues in equal density throughout the burning.

The comparative fire-retardant behaviours of the various compositions powders tested in cellulose wadding are given at tables 3.1 to 3.4 hereafter.

One can see in the following tables the effectiveness of fire-retardant powder compositions conform to the present invention with limited burning of the material.

One can see also the high efficiency of the powder as smoke-inhibitor.

Test 6.25 (Internal ref 03-18, 03-18b and 03-18t) and Test 6.26 (Internal ref 03-19 and 03-27) have been realized respectively three and two times to examine test repeatability. The surface area of the spread of the fire from test 6.25 ranges from 33 to 80%, though all three tests conducted to a 'superficially burned' result. Moreover in the corresponding tests, the weight loss of the flammable material after flame exposition and burning were respectively: 2.5%, 4.5%, 2.5% (for Tests of Internal ref. ERY 03-18, 18b and 18t). Those three weight loss were coherent with the 'superficially burned' comment in the corresponding table.

Other tests were conducted similar to tests 6.28 and 6.29 (90% Cellulose wadding and 10% by weight of flame retardant powders) were realized, replacing in the fire retardant powder the fourth additive ($ZnCl_2$ or NaCl) in same weight by the following powders: $K_2SO_4$, $K_2CO_3$, a mixture 50/50 of $KCl/MgCl_2,6H_2O$, a mixture 50/50 of $NaCl/FeSO_4,7H_2O$, a mixture 50/50 of $KCl/FeSO_4,7H_2O$, a mixture 50/50 of $MgCl_2,6H_2O/FeSO_4,7H_2O$. All the tests, except with $K_2CO_3$, were positive: with flame duration of 0.5 second, a duration of burning from 5 to 13 seconds, a 'superficially burned' material with weight loss of material after combustion of about 2.3 to 4.5%, and 'light' or 'very light' generated smoke. With $K_2CO_3$ as fourth component, the test results were the following: flame duration 0.5 s, duration of burning 975 s, 'deeply burned' material with weight loss of material after combustion of 70%. Therefore it is halogenide ions (Cl$^-$, Br$^-$, . . . ), sulfate ions ($SO_4^{--}$), or hydroxide ions (OH$^-$), rather than the cations (Na$^+$, K$^+$, Al$^{3+}$, Fe$^{2+}$, Zn$^{2+}$, Mg$^{2+}$, . . . ) of the corresponding salts that are particularly effective as flame-retardant and smoke inhibitor in synergy with monoammonium or diammonium phosphate, alkaline bicarbonate, and silica compositions of the present invention.

Should the disclosure of any patent, patent applications, and publications that are incorporated herein by reference conflict with the present description to the extent that it might render a term unclear, the present description shall take precedence.

TABLE 1

Raw materials used for making flame retardant compositions from Example 6.

| Raw materials used | Chemical formula | From | Ref. and Comment |
|---|---|---|---|
| Mono ammonium Phosphate (MAP) | $NH_4H_2PO_4$ | Thermphos | Food grade |
| Di ammonium phosphate (DAP) | $(NH_4)_2HPO_4$ | VWR | Technical grade |

TABLE 1-continued

Raw materials used for making flame retardant compositions from Example 6.

| Raw materials used | Chemical formula | From | Ref. and Comment |
|---|---|---|---|
| Sodium Bicarbonate | $NaHCO_3$ | Solvay | Bicar ® Z 0/50 - 100% <500 μm |
| Amorphous natural silica (Phonolite) | — | Hauri | VULKANITE 500 |
| Amorphous natural silica | $SiO_2$ | Solvay Rhodia | TIXOSIL 38 AB |
| Ammonium sulfate | $(NH_4)_2SO_4$ | Merck | Size Fractions >800 μm 32%, 80 < F < 800 μm 68% |
| Sodium sulfate anhydrous | $Na_2SO_4$ | VWR Prolabo | Normapur |
| Iron(II) sulfate heptahydrate | $FeSO_4, 7H_2O$ | Merck | Ph. Euro |
| Aluminium Hydroxyde (Hydrargillite) | $Al(OH)_3$ | Merck | Pure chemically |
| Sodium chloride | NaCl | ESCO | Ph. Euro |
| Potassium chloride | KCl | VWR Prolabo | Rectapur |
| Potassium bromide | KBr | VWR Prolabo | Normapur |
| Potassium carbonate | $K_2CO_3$ | VWR Prolabo | Rectapur |
| Magnesium chloride hexahydrate | $MgCl_2, 6H_2O$ | VWR Prolabo | Normapur |
| Magnesium sulfate heptahydrate | $MgSO_4, 7H_2O$ | VWR Prolabo | Normapur |
| Potassium sulfate | $K_2SO_4$ | Merck | Pure for analysis |
| Magnesium carbonate hydroxyde pentahydrate (dypingite) | $4MgCO_3, Mg(OH)_2, 5H_2O$ | VWR Prolabo | Normapur |

TABLE 2

Example 6 - Composition of tested fire-retardant powders in tests 6.1 to 6.33.

| Test nber # | Internal ref. — | MONO Ammonium Phosphate % | DI Ammonium Phosphate % | BICAR % | SILICA % | Fourth Compound Type | Fourth Compound % | Total % |
|---|---|---|---|---|---|---|---|---|
| 6.1 | 1 | — | — | — | — | — | — | 0% |
| 6.2 | 6 | — | — | 100.0% | — | — | — | 100% |
| 6.3 | 10 | — | — | 33.3% | 33.3% | Na2CO3 | 33.3% | 100% |
| 6.4 | 11 | — | — | 25.0% | 25.0% | Al(OH)3 | 50.0% | 100% |
| 6.5 | 3 | 62.5% | — | 18.8% | 18.8% | — | — | 100% |
| 6.6 | 4 | 43.8% | — | 18.8% | 18.8% | — | — | 100% |
| 6.7 | 20 | 25.0% | 25.0% | 25.0% | 25.0% | — | — | 100% |
| 6.8 | 21 | — | 62.0% | 19.0% | 19.0% | — | — | 100% |
| 6.9 | 22 | 62.0% | — | 19.0% | 19.0% | — | — | 100% |
| 6.10 | 17 | 33.0% | — | 33.0% | 33.0% | — | — | 99% |
| 6.11 | 18 | 42.9% | — | 28.6% | 28.6% | — | — | 100% |
| 6.12 | 16 | 50.0% | — | 25.0% | 25.0% | — | — | 100% |
| 6.13 | 19 | 50.0% | — | 25.0% | 25.0% | — | — | 100% |
| 6.14 | 6 | 58.8% | — | 17.6% | 17.6% | CaCO3 | 5.9% | 100% |
| 6.15 | 11 | 58.8% | — | 17.6% | 17.6% | MgSO4, 7H2O | 5.9% | 100% |
| 6.16 | 27 | 58.8% | — | 17.6% | 17.6% | KCl | 5.9% | 100% |
| 6.17 | 29 | 58.8% | — | 17.6% | 17.6% | MgCO3 dypingite | 5.9% | 100% |
| 6.18 | 13b | 58.8% | — | 17.6% | 17.6% | MgCl2, 6H2O | 5.9% | 100% |
| 6.19 | ERY 03-23 | — | — | — | — | KCl | 100.0% | 100% |
| 6.20 | ERY 03-24 | — | — | — | — | MgCl2, 6H2O | 100.0% | 100% |
| 6.21 | ERY 03-25 | — | — | — | — | ZnCl2 | 100.0% | 100% |
| 6.22 | ERY 03-26 | — | — | — | — | NaCl | 100.0% | 100% |
| 6.23 | ERY 04-20 | — | — | — | — | FeSO4, 7H2O | 100.0% | 100% |
| 6.24 | 5-4 (1) | 5.3% | 10.5% | 10.5% | 10.5% | Na2SO4 | 63.2% | 100% |
| 6.25 | ERY 03-18 18b18t | 68.0% | — | 8.0% | 4.0% | KCl | 20.0% | 100% |
| 6.26 | ERY 03-27 | 68.0% | — | 8.0% | 4.0% | FeSO4, 7H2O | 20.0% | 100% |
| 6.27 | ERY 03-20 | 68.0% | — | 8.0% | 4.0% | MgCl2, 6H2O | 20.0% | 100% |
| 6.28 | ERY 03-21 | 68.0% | — | 8.0% | 4.0% | ZnCl2 | 20.0% | 100% |
| 6.29 | ERY 03-22 | 68.0% | — | 8.0% | 4.0% | NaCl | 20.0% | 100% |
| 6.30 | ERY 03-21 | 76.0% | — | 9.0% | 5.0% | KCl | 10.0% | 100% |
| 6.31 | NG 27 | 64% | — | 7.5% | 3.8% | KBr | 25.0% | 100% |
| 6.32 | ERY 03-21 | 76.0% | — | 9.0% | 5.0% | (NH4)2SO4 | 10.0% | 100% |
| 6.33 | ERY 03-21 | 58.5% | — | 6.9% | 3.8% | (NH4)2SO4 | 30.8% | 100% |
| 6.34 | NG 3 - 8/06 | 68% | — | 8.0% | 4.0% | FeSO4•7H2O, KCl, 50/50 | 20% | 100% |
| 6.35 | NG 20 - 13/06 | 68% | — | 8.0% | 4.0% | K2SO4 | 20% | 100% |

TABLE 3.1

Example 6 - Comparative fire-retardant behaviours of non conform compositions powders tested in cellulose wadding.

| Test nber # | Internal ref: | Conform to invention | Cellulose wadding plus fire retardant composition with weight fraction of the fire retardant composition reported to the total weight of treated cellulose wadding | flame duration s | duration of burning s | surface area of the spread of the fire % | comment | Qualitative fire retardant efficacy ranking |
|---|---|---|---|---|---|---|---|---|
| 6.1 | 1 | No | Cellulose wadding alone | 8 | 600 (10 min) | 75 | deeply burned | Bad |
| 6.2 | 6 | No | 15% Sodium bicarbonate (Bicar ®) | 1 | 480 (8 min) | 95 | deeply burned | Bad |
| 6.3 | 10 | No | 4% Carbonate + 4% Bicar + 4% Vulkanite (16% total) | 1 | 120 (2 min) | 95 | deeply burned | Bad |
| 6.4 | 11 | No | 8% Aluminium Hydroxide + 4% Bicar + 4% Vulkanite (16% total) | 1 | 120 (6 min) | 90 | deeply burned | Bad |
| 6.5 | 3 | No | 10% MAP, 3% Bicar Z, 3% Vulkanite (16% total) | 1 | 46 | 70 | superficially burned | Medium |
| 6.6 | 4 | No | 7% MAP, 3% DAP, 3% Bicar Z, 3% Vulkanite (16% total) | 2 | 420 | 90 | superficially burned | Medium |
| 6.7 | 20 | No | 2.5% MAP, 2.5% DAP, 2.5% Bicar Z, 2.5% Vulkanite (10% total) | 8 | >1200 (>20 min) | 100 | deeply burned | Bad |
| 6.8 | 21 | No | 0% MAP, 6.2% DAP, 1.9% Bicar Z, 1.9%% Vulkanite (10% total) | 3 | >1200 (>20 min) | 100 | deeply burned | Bad |
| 6.9 | 22 | No | 6.2% MAP, 0% DAP, 1.9% Bicar Z, 1.9%% Vulkanite (10% total) | 4 | >1200 (>20 min) | 100 | deeply burned | Bad |

TABLE 3.2

Example 6 - Comparative fire-retardant behaviours of non-conform and conform compositions powders tested in cellulose wadding (Showing relative efficacy of fire retardant powder comprising Mono Ammonium Phosphate, Bicar and Silica with increasing amounts of powder reported to final material from 12 to 16%, and Comparative fire-retardant behaviours of deterioration or improvement when adding a fourth component non according or according the invention).

| Test nber (#) | Internal ref. | Conform to invention | Cellulose wadding plus fire retardant composition with weight traction of the fire retardant composition reported to the total weight of treated cellulose wadding | flame duration (s) | Duration of burning (s) | surface area of the spread of the fire (%) | Comment | Qualitative fire retardant efficacy ranking |
|---|---|---|---|---|---|---|---|---|
| 6.10 | 17 | No | 4% MAP + 4% Bicar + 4% Vulkanite (12% total) | 2 | 570 (9 min) | 60 | deeply burned | Insufficient |
| 6.11 | 18 | No | 6% MAP + 4% Bicar + 4% Vulkanite (14% total) | 2 | 300 (5 min) | 60 | deeply burned | Insufficient |
| 6.12 | 16 | No | 8% MAP + 4% Bicar + 4% Vulkanite (16% total) | 1 | 30 (0.5 min) | 50 | superficially burned | Good |
| 6.13 | 19 | No | 8% MAP + 4% Bicar + 4% Vulkanite (16% total) | 0 | 60 (1 min) | 40 | superficially burned | Good |
| 6.14 | 6 | No | 10% MAP + 3% Bicar + 3% Vulkanite + 1% CaCO$_3$ SOCAL U1R (17% total) | 3 | >1200 (>20 min) | 100 | deeply burned | Bad |
| 6.15 | 11 | No | 10% MAP + 3% Bicar + 3% Vulkanite + 1% MgSO$_4$, 7H$_2$O (17% total) | 1 | 341 | 90 | deeply burned | Bad |
| 6.16 | 27 | Yes | 10% MAP + 3% Bicar + 3% Vulkanite + 1% KCl (17% total) | 2 | 31 | 60 | superficially burned | Good |
| 6.17 | 29 | Yes | 10% MAP + 3% Bicar + 3% Vulkanite + 1% MgCO$_3$ dypingite (17% total) | 1 | 71 | 80 | superficially burned | Good |
| 6.18 | 13b | Yes | 10% MAP + 3% Bicar + 3% Vulkanite + 1% MgCl$_2$, 6H$_2$O (17% total) | 1 | 30 | 90 | superficially burned | Good |

TABLE 3.3

Example 6 - Comparative fire-retardant behaviours of non conform & conform compositions powders.

| Test nber (#) | Internal ref. | Conform to invention | Cellulose wadding plus fire retardant composition with weight fraction of the fire retardant composition reported to the total weight of treated cellulose wadding | Flame duration (s) | Duration of burning (s) | surface area of the spread of the fire (%) | Comment | Qualitative fire retardant efficacy | Generated Smoke |
|---|---|---|---|---|---|---|---|---|---|
| 6.19 | ERY 03-23 | No | 10% KCl | 2 | 1200 (20 min) | 95 | deeply burned | Bad | Important |
| 6.20 | ERY 03-24 | No | 10% MgCl$_2$, 6H2O | 9 | 900 | 90 | deeply burned | Bad | Light |
| 6.21 | ERY 03-25 | No | 10% ZnCl$_2$ | 1 | 1200 | 80 | deeply burned | Bad | Light |
| 6.22 | ERY 03-26 | No | 10% NaCl | 15 | 1200 | 90 | deeply burned | Bad | Medium |
| 6.23 | ERY 04-20 | No | 10% FeSO$_4$, 7H$_2$O | 0.5 | 900 | 100 | deeply burned | Bad | Important |
| 6.24 | 5-4 (1) | No | 0.5% MAP, 1% DAP, 1% Bicar, 1% Tixosil 38AB, 6% Na$_2$SO$_4$ (9.5% total) | 1 | 1740 | 100 | deeply burned | Bad | Medium |
| 6.25 | ERY 03-18 18b18t | Yes | 6.8% MAP, 0.8% Bicar, 0.4% Tixosil 38AB, 2% KCl (10% total) | 0.5 | 20, 7, 10 | 33, 80 | superficially burned | Good | Very light |
| 6.26 | ERY 03-19 03-27 | Yes | 6.8% MAP, 0.8% Bicar, 0.4% Tixosil 38AB, 2% FeSO$_4$, 7H$_2$O (10% total) | 0.5 0.5 | 8 6 | 50 80 | superficially burned | Good | Light |
| 6.27 | ERY 03-20 | Yes | 6.8% MAP, 0.8% Bicar, 0.4% Tixosil 38AB, 2% MgCl$_2$, 6H$_2$O (10% total) | 0.5 | 11 | 75 | superficially burned | Good | Light |

TABLE 3.4

Example 6 - Comparative fire-retardant behaviours of non conform compositions powders tested in cellulose wadding.

| Test nber (#) | Internal ref. | Conform to invention | Cellulose wadding plus fire retardant composition with weight fraction of the fire retardant composition reported to the total weight of treated cellulose wadding | Flame duration (s) | Duration of burning (s) | surface area of the spread of the fire (%) | Comment | Qualitative fire retardant efficacy | Generated Smoke |
|---|---|---|---|---|---|---|---|---|---|
| 6.28 | ERY 03-21 | Yes | 6.8% MAP, 0.8% Bicar, 0.4% Tixosil 38AB, 2% ZnCl$_2$ (10% total) | 0.5 | 15 | 75 | superficially burned | Good | Light |
| 6.29 | ERY 03-22 | Yes | 6.8% MAP, 0.8% Bicar, 0.4% Tixosil 38AB, 2% NaCl (10% total) | 9 | 20 | 90 | superficially burned | Good | Light |
| 6.30 | ERY 03-21 | Yes | 7.6% MAP, 0.9% Bicar, 0.5% Tixosil 38AB, 1% KCl (10% total) | 0.5 | 7 | 90 | superficially burned | Good | Very light |
| 6.31 | NG 27 | Yes | 5.1% MAP, 0.6% Bicar, 0.3% Tixosil 38AB, 2% KBr (8% total) | 0.5 | 14 | 80 | superficially burned | Good | Very light |
| 6.32 | ERY 03-21 | Yes | 7.6% MAP, 0.9% Bicar, 0.5% Tixosil 38AB, 1% (NH$_4$)$_2$SO$_4$ (10% total) | 0.5 | 7 | 80 | superficially burned | Good | Very light |
| 6.33 | ERY 03-21 | Yes | 7.6% MAP, 0.9% Bicar, 0.5% Tixosil 38AB, 4% (NH$_4$)$_2$SO$_4$ (13%) total) | 0.5 | 8 | 90 | superficially burned | Good | Very light |
| 6.34 | NG 3-8/06 | Yes | 6.8% MAP, 08% Bicar, 0.4% Tixosil 38AB, 1% FeSO$_4$•7H$_2$O, 1% KCl (10% total) | 0.5 | 5 | 80 | superficially burned | Good | Very light |

The invention claimed is:

1. A fire-retardant powder comprising:
   a. at least 30% by weight of monoammonium dihydrogen phosphate and/or di-ammonium monohydrogen phosphate,
   b. at least 5% by weight of alkaline bicarbonate,
   c. at least 3% by weight of silica, and
   d. at least 5% by weight of a compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof.

2. The powder according to claim 1, wherein the alkaline bicarbonate is potassium bicarbonate or sodium bicarbonate.

3. The powder according to claim 1, comprising at most 15% by weight of water.

4. The powder according to claim 1, comprising at most 50% by weight of said compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof.

5. The powder according to claim 1, wherein the silica is selected from the group consisting of precipitated silica, pyrogenic silica, phonolite, and combinations thereof.

6. The powder according to claim 1, wherein said compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, is selected from the group consisting of: potassium chloride, potassium bromide, potassium sulfate, magnesium chloride hexahydrate, iron(II) sulfate heptahydrate, and combinations thereof.

7. The powder according to claim 1, further comprising less than 2% by weight of boron compound expressed as boron.

8. The powder according to claim 1, being free of boron salts and/or boron acid.

9. The powder according to claim 1, being free of neurotoxic parasiticidal active principles.

10. The powder according to claim 1, wherein at least one of the components selected from the group consisting of said monoammonium phosphate, said di-ammonium phosphate, said alkaline bicarbonate, said silica, and said compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof, is present in the form of particles having a weight-average diameter of at least 80 µm.

11. The powder according to claim 1, wherein at least one of the components selected from the group consisting of monoammonium dihydrogen phosphate, di-ammonium monohydrogen phosphate; said alkaline bicarbonate; said silica;

and said compound selected from the group consisting of: sodium chloride, potassium chloride, potassium bromide, potassium sulfate, magnesium carbonate hydroxide pentahydrate, magnesium chloride hexahydrate, iron (II) sulfate heptahydrate, zinc(II) chloride, and combinations thereof, is present in the form of particles having a weight-average diameter less than or equal to 100 µm.

12. The powder according to claim 1, wherein the alkaline bicarbonate is trona or sodium bicarbonate.

13. A method of manufacturing the powder according to claim 10, comprising at least one step of simultaneous milling of at least two components of the powder selected from the group consisting of monoammonium dihydrogen phosphate, di-ammonium monohydrogen phosphate; said alkaline bicarbonate; said silica; and said compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof.

14. A method for producing a building material, comprising adding the powder of claim 1 to fibers to make a building material.

15. A building material comprising at least 5% by weight of the powder according to claim 1.

16. The building material according to claim 15, comprising at most 30% by weight of said powder.

17. The building material according to claim 15, comprising natural fibers of plant origin or of animal origin.

18. The building material according to claim 15, comprising cellulose wadding.

19. The building material according to claim 15, wherein the alkaline bicarbonate in said powder is trona, potassium bicarbonate, or sodium bicarbonate.

20. A method of manufacturing the building material according to claim 17, the manufacturing method comprising a step of simultaneous milling of the natural fibers and of the powder.

21. A method for manufacturing a fire-retardant powder, said powder comprising the following components:
    monoammonium dihydrogen phosphate and/or di-ammonium monohydrogen phosphate;
    alkaline bicarbonate;
    silica; and
    a compound selected from the group consisting of: sodium chloride, potassium chloride, potassium bromide, potassium sulfate, magnesium carbonate hydroxide pentahydrate, magnesium chloride hexahydrate, iron(II) sulfate heptahydrate, zinc(II) chloride, and combinations thereof,
    said method comprising mixing said components to form a mixture.

22. The method according to claim 21, wherein mixing comprises simultaneous milling of at least two components of the powder selected from the group consisting of:
    the monoammonium dihydrogen phosphate and/or di-ammonium monohydrogen phosphate;
    the alkaline bicarbonate;
    the silica; and
    the compound selected from the group consisting of: sodium chloride, potassium chloride, potassium bromide, potassium sulfate, magnesium carbonate hydroxide pentahydrate, magnesium chloride hexahydrate, iron (II) sulfate heptahydrate, zinc(II) chloride, and combinations thereof.

23. The method according to claim 21, wherein the alkaline bicarbonate in said powder is trona, potassium bicarbonate, or sodium bicarbonate.

* * * * *